United States Patent
Gall et al.

(10) Patent No.: US 10,791,959 B2
(45) Date of Patent: Oct. 6, 2020

(54) MAGNETIC RESONANCE APPARATUS AND METHOD FOR POSITIONING AN OBJECT ON A PATIENT POSITIONING DEVICE WITHIN AN ISOCENTER OF A MAGNETIC RESONANCE SCANNER

(71) Applicant: Siemens Healthcare GmbH, Erlangen (DE)

(72) Inventors: Peter Gall, Uttenreuth (DE); Andreas Greiser, Erlangen (DE); Dominik Paul, Bubenreuth (DE); Steffen Schröter, Fuerth (DE); Jens Thöne, Lauf an der Pegnitz (DE); Felix Wolf, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 930 days.

(21) Appl. No.: 15/160,356

(22) Filed: May 20, 2016

(65) Prior Publication Data

US 2016/0338614 A1 Nov. 24, 2016

(30) Foreign Application Priority Data

May 20, 2015 (DE) .................. 10 2015 209 237

(51) Int. Cl.
| | |
|---|---|
| *A61B 5/055* | (2006.01) |
| *A61B 5/00* | (2006.01) |
| *G01R 33/28* | (2006.01) |
| *G01R 33/30* | (2006.01) |
| *G06T 7/00* | (2017.01) |
| *G01R 33/54* | (2006.01) |

(52) U.S. Cl.
CPC ............ *A61B 5/0555* (2013.01); *A61B 5/704* (2013.01); *G01R 33/283* (2013.01); *G01R 33/307* (2013.01); *G06T 7/0012* (2013.01); *G01R 33/543* (2013.01)

(58) Field of Classification Search
CPC ......... A61B 5/055; A61B 5/0555; A61B 5/70; A61B 5/704; G01R 33/283; G01R 33/307; G01R 33/543
See application file for complete search history.

(56) References Cited

U.S. PATENT DOCUMENTS

| | | | |
|---|---|---|---|
| 2006/0164086 A1* | 7/2006 | Kohlmuller | .......... A61B 5/0555 324/307 |
| 2009/0021257 A1* | 1/2009 | Yasuhara | ............. G01R 33/283 324/318 |
| 2010/0059679 A1 | 3/2010 | Albrecht | |

(Continued)

OTHER PUBLICATIONS

Chinese Office Action dated Dec. 11, 2019, for Application No. 201610340169.0, and English translation.

*Primary Examiner* — Carolyn A Pehlke
(74) *Attorney, Agent, or Firm* — Schiff Hardin LLP

(57) ABSTRACT

A magnetic resonance apparatus has a scanner that has a patient receiving area, a position data acquisition unit, and a patient examination table of a patient positioning device. The table is movable within the patient receiving area. The position data acquisition unit detects a subarea, including an isocenter, of the patient receiving area, and provides position data to a speed regulating processor that regulates the speed of the table of patient positioning device depending on this position data.

24 Claims, 3 Drawing Sheets

(56) References Cited

U.S. PATENT DOCUMENTS

| | | |
|---|---|---|
| 2010/0182005 A1 | 7/2010 | Biber |
| 2012/0271156 A1* | 10/2012 | Bi .......................... A61B 5/055 600/415 |
| 2013/0060129 A1 | 3/2013 | Lee et al. |
| 2014/0155728 A1* | 6/2014 | Lee ........................ A61B 6/462 600/407 |
| 2014/0155736 A1* | 6/2014 | Vaidya ................. G01R 33/543 600/415 |
| 2014/0184218 A1* | 7/2014 | Heukensfeldt Jansen ................... G01R 33/546 324/309 |
| 2014/0378816 A1* | 12/2014 | Oh ....................... G01R 33/283 600/409 |
| 2015/0077113 A1 | 3/2015 | Benner |
| 2016/0128606 A1* | 5/2016 | Sakuragi ................ A61B 5/055 600/415 |
| 2017/0014203 A1* | 1/2017 | De Mathelin .......... A61B 5/055 |
| 2017/0209068 A1* | 7/2017 | Dyer ..................... A61B 90/96 |

* cited by examiner

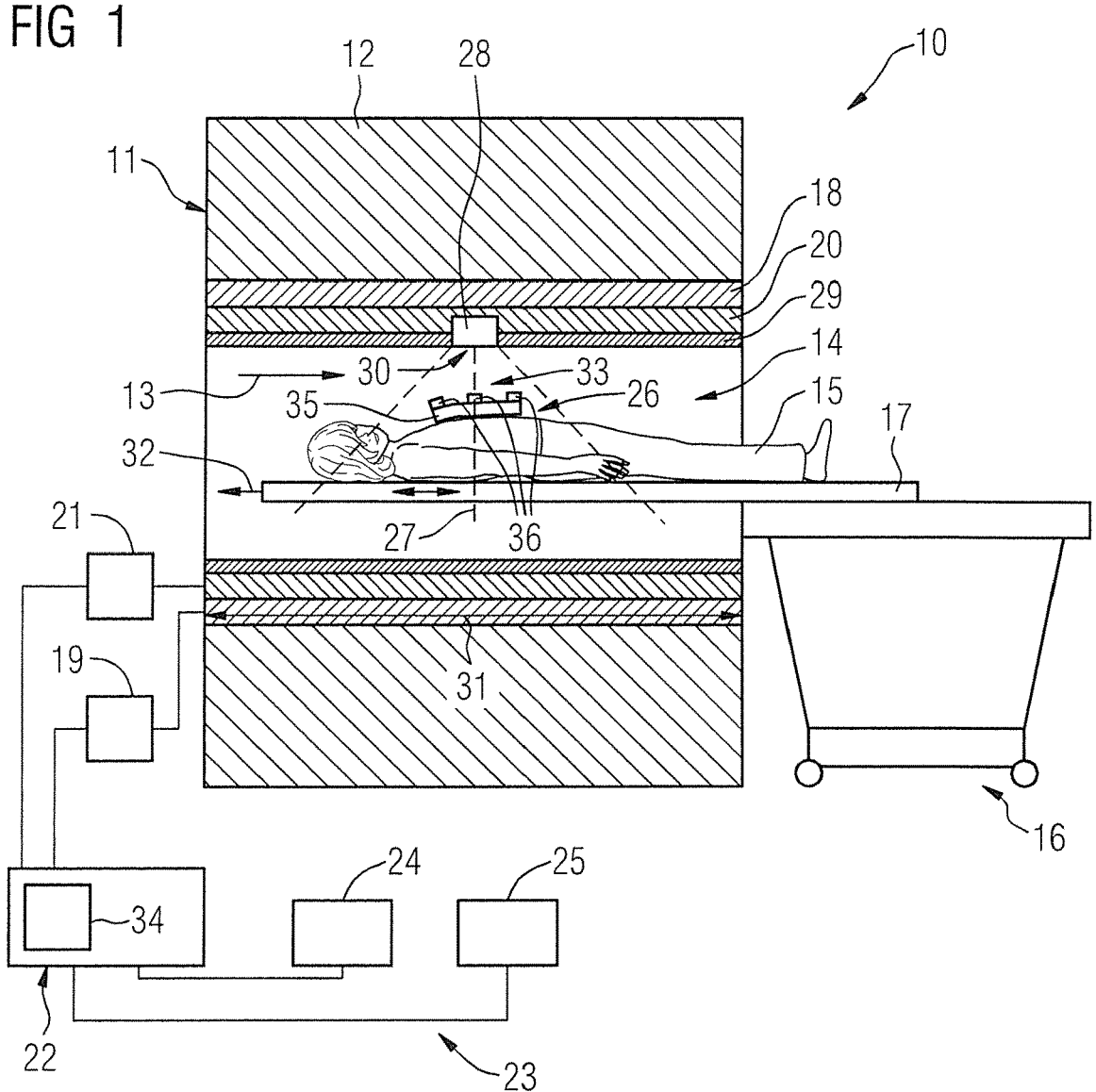
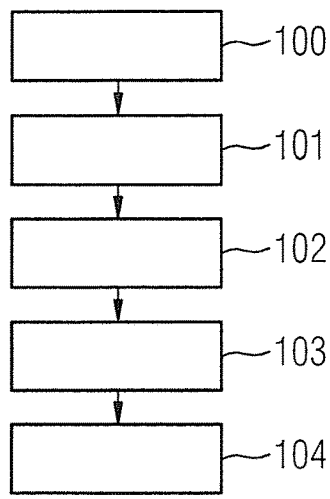

MAGNETIC RESONANCE APPARATUS AND METHOD FOR POSITIONING AN OBJECT ON A PATIENT POSITIONING DEVICE WITHIN AN ISOCENTER OF A MAGNETIC RESONANCE SCANNER

BACKGROUND OF THE INVENTION

Field of the Invention

The present invention relates to a magnetic resonance apparatus having a scanner with a patient receiving area, a position data acquisition unit, a patient examination table of a patient positioning device that is capable of movement within the patient receiving area, and a system control computer, wherein the position data acquisition computer is designed in order to acquire a subarea, including an isocenter, of the patient receiving area. The present invention furthermore relates to a method for positioning an object arranged on a patient positioning device within an isocenter of a magnetic resonance scanner.

Description of the Prior Art

A laser unit has conventionally been used for determining the position of a patient inside a magnetic resonance scanner, with which laser unit a region under examination can be marked. The laser unit is situated outside the patient receiving area, which means that the position of the patient can be determined only with the use of a movable patient positioning device. It is not possible, however, to acquire the position of the patient and/or of objects positioned on the patient within the patient receiving area, in particular in relation to an isocenter of the magnetic resonance device.

SUMMARY OF THE INVENTION

The object of the present invention is to enable simple and exact positioning of the patient and/or of an object positioned on the patient in an isocenter of a magnetic resonance scanner.

The invention is based on a magnetic resonance scanner having a patient receiving area, a position data acquisition unit, a patient examination table of a patient positioning device, which table is capable of movement within the patient receiving area, and a system control computer, wherein the position data acquisition unit is designed in order to acquire a subarea, including an isocenter, of the patient receiving area.

In accordance with the invention, the system control computer has a speed regulating processor that regulates the speed of the patient positioning device depending on position data from the position data acquisition unit. In this context a patient receiving area is to be understood as an area of the magnetic resonance scanner in which a patient and/or a region to be examined of the patient is situated for a magnetic resonance examination. Furthermore, the patient examination table of the patient positioning device, which table is capable of movement within the patient receiving area, is mounted so as to be movable in the direction of a longitudinal extent of the patient examination table within the patient receiving area. The system control computer, in particular the speed regulating processor thereof, has a processor circuit and a memory. Software and/or computer programs that, when executed by the processor circuit, enable the speed of the patient positioning device, in particular of the patient examination table, to be regulated, are stored in the memory.

The patient examination table of the patient positioning device is moved into the patient receiving area at an initial speed. The position data acquisition unit serves in this situation to acquire position data for objects that are positioned on the patient examination table. These objects can be, for example, a patient or ancillary units, such as local radio-frequency antenna units, which can be positioned on a region to be examined of the patient for the acquisition of magnetic resonance signals. On the basis of the position data for the objects, the speed of the patient examination table is regulated and/or adjusted by the speed regulating processor. The closer the object is in this case to an isocenter of the magnetic resonance scanner, the lower and/or slower is the speed of the patient examination table that can be regulated or set by the speed regulating processor.

In this context, the isocenter is understood as a point and/or a region that is situated within the patient receiving area and in which the most ideal conditions are to be found within the medical imaging scanner for the medical imaging examination during operation of the medical imaging scanner. The isocenter preferably describes a point within an isocenter region. For example, within a magnetic resonance scanner the isocenter is a point and/or a region at which the magnetic field of the magnetic resonance scanner is at its most homogeneous and which is preferably situated in the center of the basic field magnet and/or of the gradient coil unit. The isocenter for a medical imaging device is preferably determined once during the installation of the medical imaging apparatus.

In an embodiment of the invention, a medical operator can achieve particularly simple positioning of the patient examination table and, thereby also of the object and/or of the patient in the isocenter of the magnetic resonance scanner. The positioning can take place particularly exactly due to the regulation of the speed of the patient examination table. Local radio-frequency antenna units, the position of which can depend on the size and/or anatomy of the patient and/or on the positional situation of the patient and/or on the region of the patient to be examined, can be located particularly simply and, depending on the position thereof a position of the patient examination table can be set. For example, in addition to the size and/or the positional situation of the patient it is also possible to acquire the thickness of the patient by means of the position data acquisition unit, and thereby also to determine the distance of the patient from the position data acquisition unit. With a corresponding embodiment of the position data acquisition unit, for example as a camera having a wide-angle lens, it is thus also possible to reduce and/or prevent parallax errors in the position data acquisition unit.

The regulation of the speed takes place automatically and/or without operator intervention by operation of the speed regulating processor. The evaluation is preferably implemented by suitable image processing software designed to recognize the acquired objects.

Furthermore in accordance with the invention, the magnetic resonance scanner has a radio-frequency antenna unit that at least partially surrounds the patient receiving area, and the position data acquisition unit is arranged on the radio-frequency antenna unit. The radio-frequency antenna unit has a linear plain bearing unit that enables movement of the patient examination table within the radio-frequency antenna unit. The radio-frequency antenna unit is preferably formed by a radio-frequency antenna unit fixedly integrated within the basic field magnet of the magnetic resonance scanner, which is designed to generate radio-frequency signals for a magnetic resonance examination. This embodiment of the invention enables a particularly space-saving arrangement of the position data acquisition unit within the magnetic resonance scanner. Furthermore, an advantageous arrangement of the position data acquisition unit for acquiring position data for objects, in particular for the patient and/or for ancillary units arranged on the patient, such as a local radio-frequency antenna unit, can be achieved in the region of the isocenter of the magnetic resonance scanner.

In a further embodiment of the invention, the radio-frequency antenna unit has a housing that at least partially surrounds the patient receiving area and the position data acquisition unit within the housing, and/or is arranged on a side of the housing unit of the radio-frequency antenna unit facing away from the patient receiving area. This enables a space-saving arrangement of the position data acquisition unit on the radio-frequency antenna unit, which prevents any obstruction to the patient and/or the patient examination table and/or ancillary units during a movement of the patient examination table within the patient receiving area.

In a further embodiment of the invention, the radio-frequency antenna unit has a longitudinal extent and the position data acquisition unit is arranged in the center in the direction of the longitudinal extent of the radio-frequency antenna unit. This allows an advantageous and exact acquisition of position data for objects, for example a patient and/or an ancillary unit, to be achieved in a region of the isocenter of the magnetic resonance scanner. Furthermore, this allows a region of the isocenter of the magnetic resonance device to be monitored with fewer acquisition elements.

In a particularly simple and cost-effective embodiment of the position data acquisition unit, the position data acquisition unit has at least one camera. Furthermore, the use of a camera, arranged in the center of a housing unit surrounding the patient receiving area and thereby in a region of an isocenter of the magnet unit, has the advantage that any distortion in the vicinity of the target position is minimal in the position data because the object to be acquired by the camera is situated substantially centrally in an acquisition region of the position data acquisition unit. Other embodiments of the position data acquisition unit that are considered expedient to those skilled in the art are also possible. For example, the position data acquisition unit can have more than one camera and/or the position data can be acquired by alternative acquisition methods, such as by RFID (radio-frequency identification), ultrasound or by a Hall probe.

The camera can have a wide-angle lens and/or a fisheye lens. In this context a wide-angle lens means a lens that has an angle of view greater than 60°, preferably greater than 75° and particularly advantageously greater than 100°. Most preferably, the wide-angle lens has an angle of view of approx. 120°. A fisheye lens is furthermore to be understood as a wide-angle lens that images straight lines that continue outside the image center in curved fashion. Preferably, the fisheye lens also has an angle of view greater than 60°, preferably greater than 75° and particularly advantageously greater than 100°. Most preferably the fisheye lens has an angle of view of approx. 120°. This embodiment of the invention makes it possible to acquire and/or to monitor a region which encompasses the isocenter of the magnetic resonance scanner completely and/or in its entirety with only a single camera. It is also possible to compensate for parallax errors, which in turn enables as exact and precise positioning as possible of the objects in the isocenter of the magnetic resonance device.

In a further embodiment of the invention, the position data acquisition unit acquires position data for an object which is positioned on the patient positioning device. In this manner, objects that may occupy different positions on the patient positioning device, in particular on the patient examination table, can be positioned within the isocenter of the magnetic resonance scanner. The object can be a patient. Alternatively or additionally, the object may be an ancillary unit, such as a local radio-frequency antenna.

In order to facilitate acquisition of the object, in particular of a subregion to be examined of the patient and/or of an ancillary unit covering the subregion to be examined, such as a local radio-frequency antenna unit, the object is given an object-specific pattern in accordance with the invention. In this context, an object-specific pattern means a pattern that can be used to effect an unambiguous identification of the object in the acquired position data. The object-specific pattern can be a shape and/or a surface design of the object. It is also conceivable for the object-specific pattern to be generated by additional marker elements that are situated on a surface of the object.

With the object-specific pattern, it is also possible to recognize a positional situation and/or position of a local radio-frequency antenna unit on the patient on the basis of the acquired position data. On the basis of the positional situation and/or position of the local radio-frequency antenna unit, it is subsequently possible to deduce an application, and a position of the patient examination table can be determined for positioning the local radio-frequency antenna unit in a region of the isocenter. For example, in the case of a particular arrangement of the local radio-frequency antenna unit on the patient, positioning is to be effected with respect to an edge region and/or a region within the isocenter differing from a central region of the local radio-frequency antenna unit. The speed regulating unit has correspondingly designed image processing software for performing such an acquisition and evaluation.

Furthermore, by the use of a suitable two-dimensional geometric pattern that is situated on the object it is also possible to reduce and/or prevent distortion in the acquired position data at the edge of an acquisition region of the position data acquisition unit.

In a further embodiment of the invention, the speed regulating processor regulates the speed of the patient examination table depending on the distance of the acquired object in relation to the isocenter. This enables a particularly simple positioning of the patient examination table, and thereby also of the patient, within the magnetic resonance scanner, such that the workflow and/or workload can be simplified for a medical operator. The positioning can be implemented very precisely due to the automatic regulation of the speed of the patient examination table by the speed regulating processor. The distance of the object is, for example, the distance of a region under examination of a patient and/or the distance of a central region of a local radio-frequency antenna unit, etc. in relation to the isocenter.

In a further embodiment of the invention, the speed regulating processor slows the speed of the patient examination table as the distance of the acquired object becomes smaller in relation to the isocenter. A reduction in the speed of the patient examination table the closer the object is to the isocenter enables a precise positioning of the object within the isocenter of the magnetic resonance scanner for a pending magnetic resonance examination. The distance of the object in relation to the isocenter is determined and/or ascertained by the speed regulating processor on the basis of the position data. Preferably, the speed regulating unit is designed such that a continuous adjustment and/or regulation of the speed of the patient examination table takes place, with this continuous adjustment and/or regulation of the speed of the patient examination table depending on the distance of the object, in particular a local radio-frequency antenna unit, in relation to the isocenter.

The invention furthermore encompasses a method for positioning an object arranged on a patient examination table of a patient positioning device within an isocenter of a magnetic resonance scanner that has a patient receiving area, a patient positioning device, a position data acquisition unit, a patient examination table that is movable within the patient receiving area, and a system control computer, wherein the scanner is designed in order to acquire magnetic resonance data from a subarea, including an isocenter, of the patient receiving area and the system control computer has a speed regulating processor that regulates the speed of the patient examination table depending on position data from the position data acquisition unit.

The method includes the steps of positioning an object on the patient examination table of the patient positioning device, moving the patient examination table together with the object into the patient receiving area at an initial speed, acquiring position data with the position data acquisition unit, evaluating the acquired position data in the speed regulating processor, wherein the distance of the object in relation to the isocenter is ascertained, and regulating the speed of the patient examination table with the speed regulating processor depending on the distance of the object in relation to the isocenter, the regulation of the speed involving an adjustment of the initial speed.

By this method it is possible for a medical operator to achieve particularly simple positioning of the patient examination table, and thereby of the object and/or of the patient, within the isocenter of the magnetic resonance scanner. The positioning can be implemented precisely due to the regulation of the speed of the patient examination table. Local radio-frequency antenna units, the position of which can depend on the size of the patient and/or on the positional situation of the patient and/or on the region of the patient to be examined, can be located particularly simply and depending on the position thereof, the position of the patient examination table can be set. Preferably, the regulation of the speed is effected automatically and/or without operator intervention by the speed regulating processor. The evaluation is preferably effected by suitable image processing software designed to recognize the objects that are acquired.

The advantages of the method according to the invention for positioning an object arranged on a patient examination table of a patient positioning device within an isocenter of a magnetic resonance scanner essentially correspond to the advantages of the magnetic resonance apparatus according to the invention as explained above in detail. Features, advantages and alternative embodiments mentioned above apply as well to the method.

In accordance with the invention, the regulated speed is less than or equal to the initial speed. This enables particularly precise setting of the position of the object in relation to the isocenter, due to a slower movement of the patient examination table in the region of the isocenter.

In a further embodiment of the invention, the regulated speed can attain a minimum as soon as the object positioned on the patient examination table is located within the isocenter. Preferably, the minimum for the regulated speed here comprises no movement of the patient examination table. The object positioned on the patient examination table is preferably located within the isocenter when a central region and/or a relevant region of the object is located within the isocenter. In this manner, the patient examination table can be precisely within the isocenter with minimal effort by a medical operator. Complex manual setting of the exact position is thus unnecessary for the medical operator.

In the method according to the invention, the regulated speed of the patient examination table can be slower, the smaller the distance of the object is to the isocenter. The reduction in the speed of the patient examination table the closer the object is to the isocenter enables precise positioning of the object within the isocenter of the magnetic resonance scanner for a pending magnetic resonance examination.

In a further embodiment of the invention, the movement of the patient examination table into the patient receiving area is effected automatically. Preferably, the movement of the patient examination table into the patient receiving area is controlled and/or regulated by the system control computer, in particular by the speed regulating processor thereof. A start signal, which begins the movement of the patient examination table into the patient receiving area, is preferably given manually by the medical operator for safety reasons. In this manner the error susceptibility of moving the patient examination table and/or regulating the speed of the patient examination table can be reduced. In this situation the position data acquisition unit can be activated for position acquisition automatically by the speed regulating processor as soon as the patient examination table moves into the patient receiving area.

In a further embodiment of the invention, the recognition of the object positioned on the patient examination table can be effected by pattern recognition from the acquired position data. Preferably, the pattern recognition is implemented by the speed regulating processor, which for this purpose has appropriate image processing software for pattern recognition of objects, in particular of local radio-frequency antennas. The object determination in the acquired position data can be achieved by pattern recognition of the image processing software. Furthermore, the acquisition time for acquisition and/or recognition of the object can be reduced by means of a pattern specific to an object. This also makes it possible to reduce an acquisition region for the position data acquisition unit. The pattern recognition can be achieved on the basis of the shape of the object, in particular of the local radio-frequency antenna unit. The pattern recognition also can be implemented on the basis of a pattern, applied on the object, which is specific to and/or characteristic of the object and which is arranged on a side of the object facing the position data acquisition unit. This surface can be, for example, a surface of a local radio-frequency antenna unit facing the position data acquisition unit. It is furthermore also conceivable for the pattern applied on the object to be generated by at least one marker element, preferably multiple marker elements, which may be arranged in distributed fashion on the surface of the object. Preferably, the acquisition and/or determination of the object commences as soon as at least a portion of the object enters an acquisition region of the position data acquisition unit and/or a marker element arranged on the object enters the acquisition region of the position data acquisition unit.

Alternatively or additionally, a selection of the object from an object list can be made prior to a movement of the patient examination table into the patient receiving area. The selection of the object from the object list can be made, for example, by inserting a connector of a local radio-frequency antenna unit, and an assignment to the local radio-frequency antenna unit can be made automatically by the system control computer by recognition of a connection contact. This is advantageous in the case of local radio-frequency antenna units that have an unambiguous position in relation to the patient. If a local radio-frequency antenna unit is used that can be displayed at different positions on the patient, the object selection is initially effected automatically by the system control computer, with a further object list of the possible positions for manual selection being displayed to a medical operator. The selection is then made manually from the object list by the medical operator. A target position for the patient examination table can be determined by selecting the object from an object list. This means that the position data acquisition unit can be activated only when the selected object enters the acquisition region of the position data acquisition unit.

In a further embodiment of the invention, a target position for the patient examination table is determined based on the selection of the object, wherein the target position for the patient examination table is optimized based on the position data from the position data acquisition unit. Preferably, the optimization of the target position of the patient examination table is effected by means of the speed regulating processor. The target position of the patient examination table is determined based on a selection of an object from the object list. A registration of the patient is preferably required in order to ascertain the target position so that the target position can be ascertained depending on the anatomy of the patient. The target position here is therefore independent of a position of the patient and/or of the actual (exact) position of, for example, a local radio-frequency antenna unit on the patient. Using the position data from the position data acquisition unit, the target position is automatically adjusted to the actual position and/or positional situation of the patient automatically by the speed regulating processor.

The invention furthermore encompasses a non-transitory, computer-readable data storage medium, having program code that can be loaded directly in a memory of a programmable system control computer of a magnetic resonance apparatus. This control computer has program resources in order to perform a method for positioning an object arranged on a patient positioning device within an isocenter of a magnetic resonance apparatus in accordance with the invention, when the program code is executed in the system control computer of the magnetic resonance apparatus. The computer code may require program resources such as libraries and auxiliary functions, in order to implement the corresponding embodiments of the method. The program code may be source code, which still needs to be compiled and linked, or which only needs to be interpreted, or executable software code which only needs to be loaded into the corresponding computing unit for execution.

BRIEF DESCRIPTION OF THE DRAWINGS

FIG. 1 is a schematic illustration of a magnetic resonance apparatus according to the invention.

FIG. 2 is a flowchart of a method according to the invention for positioning an object arranged on a patient examination table of a patient positioning device within an isocenter of a magnetic resonance apparatus.

DESCRIPTION OF THE PREFERRED EMBODIMENTS

Figure 3:
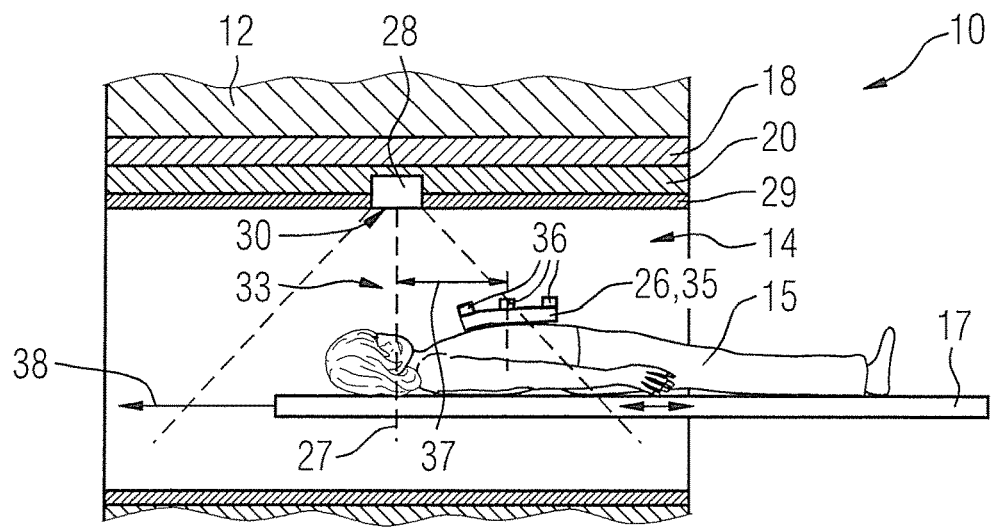
FIG. 3 shows a first position of an object within a patient receiving area.

FIG. 1 illustrates a magnetic resonance 10. The magnetic resonance apparatus 10 has a scanner 11 having a superconducting basic field magnet 12 that generates a strong and homogenous basic magnetic field 13. The magnetic resonance scanner 11 has a patient receiving area 14 for receiving a patient 15. The patient receiving area 14 in the present exemplary embodiment is cylindrical in design and is cylindrically surrounded in a circumferential direction by the scanner 11. In principle, a design of the patient receiving area 14 differing therefrom is conceivable. The patient 15 can be moved into the patient receiving area 14 by a patient positioning device 16 of the magnetic resonance apparatus 10. To this end, the patient positioning device 16 has a patient examination table 17 designed so as to be movable within the patient receiving area 14.

The scanner 11 furthermore has a gradient coil arrangement 18 in order to generate magnetic field gradients that are used for position encoding during imaging. The gradient coil arrangement 18 is controlled by a gradient control processor 19 of the magnetic resonance apparatus 10. The scanner 11 furthermore has a radio-frequency (RF) antenna 20 that radiates RF energy that excites nuclear spins in the patient 15 so as to deviate from the polarization established in the basic magnetic field 13 generated by the basic field magnet 12. The radio-frequency antenna 20 is here fixedly integrated within the scanner 11. The radio-frequency antenna 20 is controlled by a radio-frequency antenna control processor 21 of the magnetic resonance apparatus 10 and so as to radiate radio-frequency magnetic resonance sequences into an examination area, which is essentially formed by the patient receiving area 14 of the scanner 11.

The magnetic resonance apparatus 10 has a system control computer 22 in order to control the basic field magnet 12, the gradient control processor 19 and for controlling the radio-frequency antenna control processor 21. The system control computer 22 provides central control of the magnetic resonance apparatus 10, such as for performing a predetermined imaging gradient echo sequence. The system control computer 22 has an evaluation processor (not shown) for evaluating medical image data acquired during the magnetic resonance examination.

The magnetic resonance apparatus 10 furthermore has a user interface 23 connected to the system control computer 22. Control information, such as imaging parameters, and reconstructed magnetic resonance images, can be displayed on a display monitor 24, for example on at least one monitor, of the user interface 23 for a medical operator. The user interface 23 furthermore has an input unit 25, which can be used by the medical operator to enter information and/or parameters during a measurement operation.

In order to position an object 26 arranged on the patient examination table 17 of the patient positioning device 16, for example a region to be examined of the patient 15 and/or an ancillary unit, within the isocenter 27 of the magnetic resonance scanner 11, the magnetic resonance apparatus 10 has a position data acquisition unit 28 which is designed to detect the subarea of the patient receiving area 14 surrounding the isocenter 27. In this situation the isocenter 27 is formed by a region of the patient receiving area 14 surrounded by the scanner 11, where the basic magnetic field is as homogeneous as possible.

In the exemplary embodiment, the position data acquisition unit 28 is a single camera. Designs of the position data acquisition unit 28 differing therefrom are also conceivable in an alternative embodiment of the invention. The camera in this embodiment has a wide-angle lens or a fisheye lens, with the wide-angle lens or the fisheye lens being directed at the isocenter 27 of the patient receiving area 14 such that position data for the object 26 positioned on the patient examination table 17 within the isocenter 27 can be acquired by the position data acquisition unit 28. The lens arranged within the position data acquisition unit 28 has an angle of view that is greater than 60°, preferably greater than 75° and particularly advantageously greater than 100°. Most preferably the lens within the position data acquisition unit 28 has an angle of view of approximately 120°.

The position data acquisition unit 28 is arranged on the radio-frequency antenna 20. As noted above, the radio-frequency antenna 20 surrounds the patient receiving area 14, and thus also the region of the isocenter 27 of the patient receiving area 14, in cylindrical fashion. The radio-frequency antenna 20 here has a housing 29 facing the patient receiving area 14. The housing 29 surrounds the patient receiving area 14, and thus also the region of the isocenter 27 of the patient receiving area 14, in cylindrical fashion. The position data acquisition unit 28 is at least partially integrated within the housing 29 and at least partially arranged on a side of the housing unit 29 facing away from the patient receiving area 14. For this purpose the housing 29 has a transparent subarea 30 (i.e., transparent for position detection "seen by" the position data acquisition unit 28).

The radio-frequency antenna 20 has a longitudinal extent 31 that is essentially the same as the direction 32 in which the patient examination table 17 is moved into the patient receiving area 14. The transparent subarea 30 of the housing 29 of the radio-frequency antenna 20 is arranged in the center in the direction of the longitudinal extent 31 of the radio-frequency antenna 20 such that an acquisition region 33 of the position data acquisition unit 28 can optimally encompass the isocenter 27 of the scanner 11. The position data acquisition unit 28 is thus also arranged in the center in the direction of the longitudinal extent 31 of the radio-frequency antenna 20 on the housing 29 of the radio-frequency antenna 20.

The magnetic resonance apparatus 10, in particular the system control computer 22 thereof, furthermore has a speed regulating processor 34 that regulates the speed of the patient examination table 17 based on position data from the position data acquisition unit 28 that represent the position detected thereby. Here the speed regulating processor 34 is designed (configured) to regulate the speed of the patient examination table 17 depending on the distance of the object 26 acquired by the position data acquisition unit 28 in relation to the isocenter 27 of the scanner 11. In this situation, the speed regulating processor 34 sets a slower speed of the patient examination table 17, the smaller the distance of the object 26 acquired by the position data acquisition unit 28 is in relation to the isocenter 27.

The acquisition of the object 26 arranged and/or positioned 26 on the patient examination table 17, for example a subregion to be examined of the patient 15 and/or an ancillary unit arranged on the patient 15, in particular a local radio-frequency antenna 35, can be effected by pattern recognition, for this purpose the speed regulating processor 34 has suitable software and/or computer programs, such as image processing algorithms, which are stored in a memory (not illustrated) of the speed regulating processor 34 and/or of the system control computer 22.

FIG. 2 shows a flowchart of a method according to the invention for positioning an object 26 arranged on the patient examination table 17 of the patient positioning device 16 within the isocenter 27 of the magnetic resonance scanner 11. The method is controlled by the system control computer 22 together with the speed regulating processor 34. To this end, the system control computer 22 and/or the speed regulating processor 34 has control software and/or control programs that are stored in the memory (not illustrated) of the system control computer 22 and/or of the speed regulating processor 34.

In a first method step 100, positioning of an object 26 on the patient examination table 17 of the patient positioning device 16 takes place. The positioning can in this situation includes positioning a patient 15 and/or also positioning an ancillary unit, for example a local radio-frequency antenna 35 on the patient 15. In particular, in the case of one or more local radio-frequency antenna 35, the position of which is freely selectable on the patient examination table 17, the position of the local radio-frequency antenna 35 is often dependent on the region to be examined of the patient 15 and/or the positional situation of the patient 15 and/or the size of the patient 15, which means that the local radio-frequency antenna 35 can assume different positions in relation to the patient examination table 17 for different patients 15 and/or different examinations. A local radio-frequency antenna 35 that are assigned a fixed position on the patient examination table 17, such as a local head antenna, always have the same position in relation to the patient examination table 17 regardless of the size of the patient 15. Positioning of the object 26 is effected manually by a medical operator.

After the object 26 has been positioned on the patient examination table 17, a selection of the object 26 is made from an object list before the patient examination table 17 is moved into the patient receiving area 14. The selection can be effected automatically and/or without operator intervention by means of the system control computer 22, in particular by the speed regulating processor 34, provided that the object 26 comprises a local radio-frequency antenna 35 which is acquired by means of a connection contact (not illustrated in detail) between the local radio-frequency antenna 35 and the patient examination table 17. Provided that the local radio-frequency antenna 35, in particular the position of the local radio-frequency antenna 35, can be adjusted flexibly to the size and/or the positional situation of the patient 15, the selection of the object 26, in particular a position of the object 26 in relation to the patient examination table 17, is effected manually by the medical operator, where a preselection is already effected automatically and/or without operator intervention by the speed regulating processor 34, by which the local radio-frequency antenna 35 has already been determined or selected and only the exact position thereof needs to be defined by the medical operator.

On the basis of the selection of the object 26, in particular of the local radio-frequency antenna 35, a target position is determined for the patient examination table 17. The determination of the target position is preferably effected automatically and/or without operator intervention by means of the speed regulating processor 34. In this situation the target position defines a final position of the patient examination table 17 within the patient receiving area 14, in which case the object 26 positioned on the patient examination table 17, in particular a local radio-frequency antenna 35, is situated at least partially in the region of the isocenter 27 in the target position of the patient examination table 17.

In a subsequent method step 200, the patient examination table 17 is moved together with the object 26 into the patient receiving area 14 at an initial speed. The movement of the patient examination table 17 into the patient receiving area 14 is effected automatically and/or without operator intervention by means of the speed regulating processor 34. As a result of the patient examination table 17 beginning to move into the patient receiving area 14 the position data acquisition unit 28 is also activated automatically and/or without operator intervention for position data acquisition.

In a further method step 102, position data are acquired by the position data acquisition unit 28 and transferred to the speed regulating processor 34 for position data evaluation. In a subsequent method step 103, the acquired position data are evaluated by means of the speed regulating processor 34, to identify the distance of the object 26, in particular of the local radio-frequency antenna 35, in relation to the isocenter 27 is ascertained.

Figure 6:
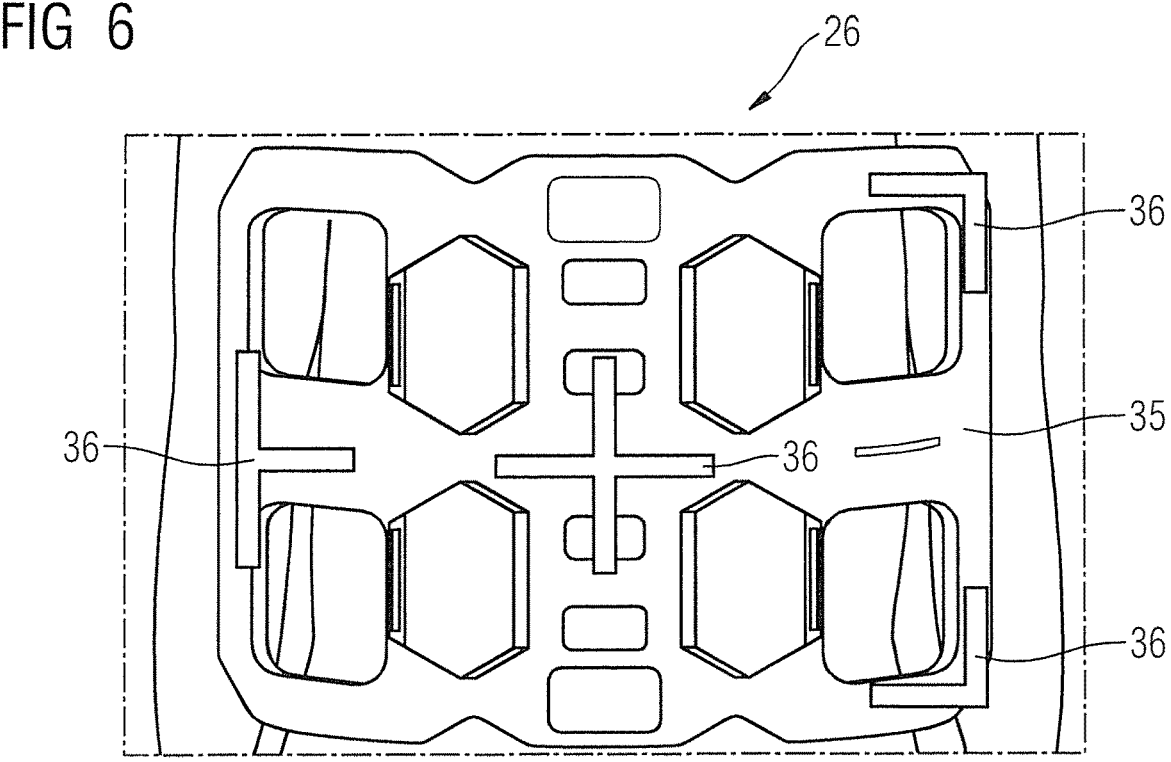
FIG. 6 shows a first exemplary embodiment of a local radio-frequency antenna unit having an object-specific pattern.
Figure 7:
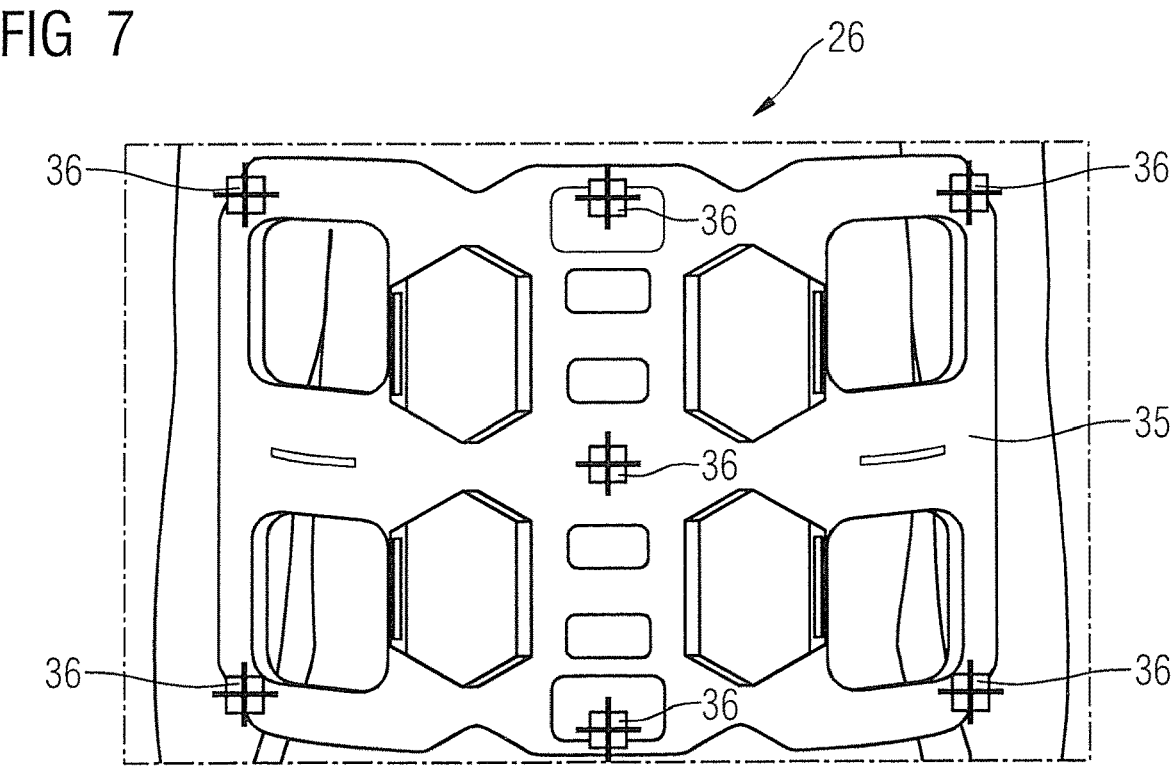
FIG. 7 shows a second exemplary embodiment of a local radio-frequency antenna unit having an object-specific pattern.

During the evaluation of the position data, a recognition and/or determination of the object 26 in the position data is initially effected by means of the speed regulating processor 34. The recognition and/or determination of the object 26 positioned on the patient examination table 17 can in this situation be effected by pattern recognition. The pattern recognition can be implemented, for example, on the basis of a shape of the local radio-frequency antenna 35. For the pattern recognition, it is also possible for a pattern to be provided on the object 26 that is characteristic of the object 26, in particular the local radio-frequency antenna 35, and/or of the position of the local radio-frequency antenna 35. The characteristic pattern can in this situation be arranged on the local radio-frequency antenna 35. FIGS. 6 and 7 illustrate two exemplary embodiments of a characteristic pattern of a local radio-frequency antenna 35 which is designed as a local body antenna unit. The characteristic patterns of each local radio-frequency antenna 35 are formed in the present exemplary embodiment as individual marker elements 36 on a surface of the local radio-frequency antenna 35.

FIG. 6 illustrates the local body antenna unit having large marker elements 36 which mark a center and an edge of the local body antenna unit on a large scale.

FIG. 7 illustrates the local body antenna unit having many small marker elements 36. The many small marker elements 36 likewise mark a center and an edge region of the local body antenna unit, where the edge region is provided with more marker elements 36 than are used in the exemplary embodiment in FIG. 6.

The acquisition of the position data for the local radio-frequency antenna 35 begins as soon as one of the marker elements 36 enters the detection region and/or enters the acquisition region 33 of the position data acquisition unit 28. On the basis of the position data for a recognized object 26, a determination of a distance 37 of the local radio-frequency antenna 35 in relation to the isocenter 27 of the scanner 11 is effected in the further method step 103. The distance 37 between the local radio-frequency antenna 35 and the isocenter 27 can in this situation be a distance 37 of a central region of the local radio-frequency antenna 35 from the isocenter 27.

In the further method step 103, an optimization of the selected and/or determined target position is effected by the speed regulating processor 34 on the basis of the acquired position data. An exact position of the local radio-frequency antenna 35 is determined here on the basis of the position data and, if necessary, the target position of the patient examination table 17 is corrected and/or optimized.

In a further method step 104, a regulation of the speed of the patient examination table 17 is effected by the speed regulating processor 34, with the regulation of the speed being implemented based on the distance 37 of the local radio-frequency antenna 35 in relation to the isocenter 27. Here the initial speed is adjusted and/or set by the speed regulating processor 34 dependent on the distance 37 of the local radio-frequency antenna 35 in relation to the isocenter 27.

Figure 4:
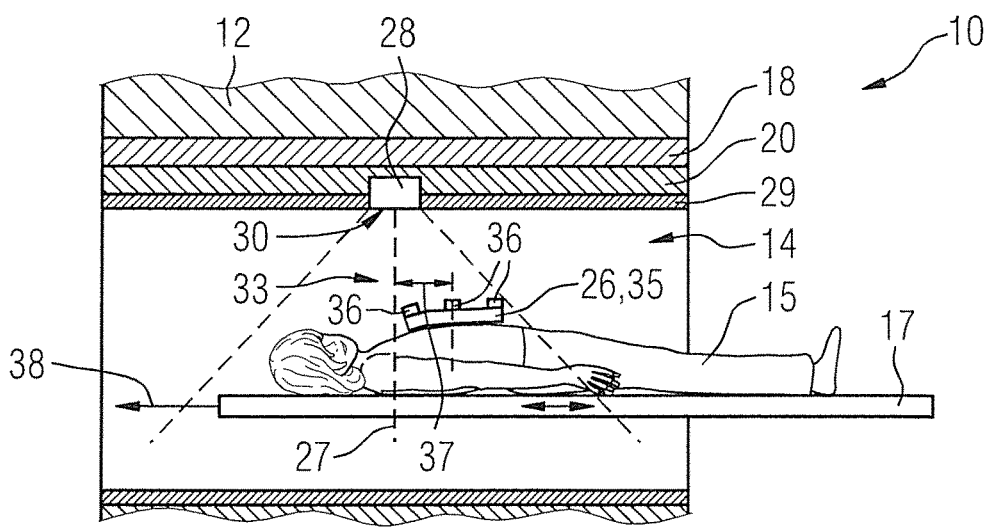
FIG. 4 shows a second position of the object within the patient receiving area at a closer distance to an isocenter of the magnetic resonance apparatus.
Figure 5:
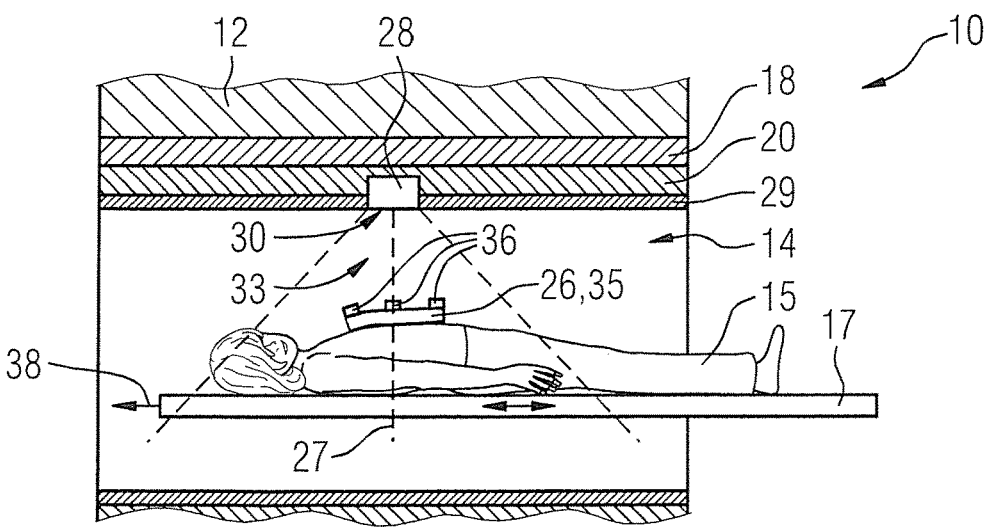
FIG. 5 shows a third position of the object within the patient receiving area, where the object is arranged within the isocenter of the magnetic resonance apparatus.

The speed regulated by the speed regulating processor 34 for the patient examination table 17 is in this situation less than or equal to the initial speed of the patient examination table 17. The speed regulated by the speed regulating processor 34 is made less, the smaller the distance of the object 26, in particular of the local radio-frequency antenna 35, is in relation to the isocenter 27. This is illustrated in FIGS. 3 to 5. The regulated speed 38 of the patient examination table 17 in FIGS. 3 and 4 is represented by means of arrows, where the larger the arrow size, the greater is the regulated speed 38 represented of the patient examination table 17.

In FIG. 3 the patient examination table 17 with the local radio-frequency antenna 35 positioned thereon enters the acquisition region 33 and/or detection region of the position data acquisition unit 28. The patient examination table 17 is moving here at the initial speed. The distance 37 between the local radio-frequency antenna 35 and the isocenter 27 is calculated on the basis of the acquired position data. The distance 37 between the local radio-frequency antenna 35 and the isocenter 27 is still of a magnitude such that the initial speed is still maintained.

In FIG. 4 the patient examination table 17 with the local radio-frequency antenna 35 positioned thereon has already advanced further into the acquisition region 33 and/or detection region of the position data acquisition unit 28. The acquired position data is used to determine the distance 37 between the local radio-frequency antenna 35 and the isocenter 27, where the distance 37 between the local radio-frequency antenna 35 and the isocenter 27 in FIG. 4 is less than in FIG. 3. On account of the small distance 37 between the local radio-frequency antenna 35 and the isocenter 27, the speed 38 regulated by the speed regulating processor 34 is less than the initial speed.

In FIG. 5 the central region of the local radio-frequency antenna 35 is situated directly in the isocenter 27 of the scanner 11. The speed 38 regulated by the speed regulating processor 34 is regulated to a minimum, where the patient examination table 17 at a standstill constitutes the minimum in the present exemplary embodiment. The speed of the patient examination table here is 0 m/s.

The smaller a distance 37 is between the object 26 positioned on the patient examination table 17 and the isocenter 27 of the scanner 11, the slower is the movement of the patient examination table 17 effected by the speed regulating processor 34 toward the isocenter 27 of the scanner 11, which means that particularly simple and exact positioning of the object 26, in particular of a local radio-frequency antenna 35, within the isocenter 27 can always be effected for a pending magnetic resonance examination.

Although modifications and changes may be suggested by those skilled in the art, it is the intention of the inventors to embody within the patent warranted hereon all changes and modifications as reasonably and properly come within the scope of their contribution to the art.

We claim as our invention:

1. A magnetic resonance (MR) apparatus comprising:
    an MR data acquisition scanner having a patient receiving area therein, said patient receiving area having an isocenter;
    a patient positioning device having a patient examination table that is movable within said patient receiving area;
    a position data acquisition detector that is separate from the MR data acquisition scanner, the position data acquisition detector having a detection field of view, which includes said isocenter, in which said position data acquisition detector detects position data associated with an object that is positioned on a patient positioned on the patient examination table, the object being a physical ancillary unit associated with the MR apparatus that is separate from the patient, the object including a predetermined characteristic pattern formed thereon that is detectable by the position data acquisition detector; and
    a speed regulating processor, provided with detected position data from the position data acquisition detector, configured to regulate a speed of movement of said patient examination table in said patient receiving area dependent on said detected position data,
    wherein the predetermined characteristic pattern formed on the object indicates a center and an edge region of the physical ancillary unit associated with the MR apparatus.

2. An MR apparatus as claimed in claim 1 wherein said MR data acquisition scanner comprises a radio-frequency (RF) antenna that at least partially surrounds said patient receiving area and wherein said position data acquisition detector is situated on said RF antenna.

3. An MR apparatus as claimed in claim 2 wherein said RF antenna comprises a housing that also at least partially surrounds said patient receiving area, and wherein said position data acquisition detector is situated at a location relative to said housing selected from the group consisting of a location within said housing, and a location at a side of said housing facing away from said patient receiving area.

4. An MR apparatus as claimed in claim 2 wherein said RF antenna has a longitudinal extent along said MR data acquisition scanner, and wherein said position data acquisition detector is situated in a center of a direction of said longitudinal extent of said RF antenna.

5. An MR apparatus as claimed in claim 1 wherein said position data acquisition detector comprises at least one camera.

6. An MR apparatus as claimed in claim 5 wherein said at least one camera comprises a lens selected from the group consisting of a wide-angle lens and a fish eye lens.

7. An MR apparatus as claimed in claim 1, wherein said speed regulating unit is configured to regulate the speed of said patient examination table dependent on a distance of the object, as detected by said position data acquisition detector, relative to said isocenter.

8. An MR apparatus as claimed in claim 7 wherein said speed regulating processor is configured to regulate said speed of said patient examination table so as to be slower as the distance of the object relative to the isocenter becomes smaller.

9. An MR apparatus of claim 1, wherein the characteristic pattern included as part of the object includes multiple marker elements arranged in distributed fashion on the surface of the object.

10. An MR apparatus of claim 9, wherein the position data acquisition detector is configured to begin acquisition of the position data upon one of the multiple marker elements entering the detection field of view.

11. An MR apparatus of claim 1, wherein the speed regulating processor is configured to execute a pattern recognition algorithm to identify the object via the characteristic pattern in accordance with a shape of a local radio-frequency body antenna.

12. An MR apparatus of claim 1, wherein the position data acquisition detector is configured to determine, using the detected position data obtained via the predetermined characteristic pattern formed on the object, a position of the patient examination table for positioning the physical ancillary unit in a region of the isocenter of the patient receiving area using the detected position data.

13. An MR apparatus of claim 1, wherein:
    the predetermined characteristic pattern formed on the object includes multiple marker elements arranged in distributed fashion on the surface of the object,
    one or more first marker elements from among the multiple marker elements indicate the center region of the physical ancillary unit,
    one or more second marker elements from among the multiple marker elements indicate the edge region of the physical ancillary unit, and
    the one or more first marker elements are different than the one or more first marker elements.

14. A method for positioning an object on a movable patient examination table of a patient positioning device, relative to an isocenter of a patient receiving area of a magnetic resonance (MR) data acquisition scanner, said method comprising:
    placing an object that is positioned on a patient positioned on the movable patient examination table of the patient positioning device, the object being a physical ancillary unit associated with the MR apparatus that is separate from the patient, the object including a predetermined characteristic pattern formed thereon;
    operating the patient positioning device with a speed regulating processor to move the patient examination table, with the object thereon, into the patient receiving area at an initial speed;
    detecting position data associated with the object with a position data acquisition detector that is separate from the MR data acquisition scanner by detecting the characteristic pattern on the object, while the patient examination table with the object thereon is moving in the patient receiving area;
    in said speed regulating processor, evaluating the acquired position data to determine a distance of the object on the patient examination table in relation to the isocenter; and
    from said speed regulating processor, operating the patient positioning device to regulate the speed of movement of the patient examination table dependent on said distance of the object relative to the isocenter, by adjusting said initial speed, wherein the predetermined characteristic pattern formed on the object indicates a center and an edge region of the physical ancillary unit associated with the MR apparatus.

15. A method as claimed in claim 14 comprising regulating said speed of said patient examination table to be less than or equal to said initial speed.

16. A method as claimed in claim 14 comprising regulating said speed of said patient examination table so as to limit the speed of said patient examination table to a threshold speed as soon as said object that is positioned on the patient positioned on the patient examination table is situated within the isocenter.

17. A method as claimed in claim 14 comprising regulating the speed of the patient examination table to be slower as the distance of the object with respect to the isocenter becomes smaller.

18. A method as claimed in claim 14 comprising automatically effecting said movement of the patient examination table into the patient receiving area at said initial speed.

19. A method as claimed in claim 14 comprising activating operation of said position data acquisition detector as soon as said patient examination table moves into said patient receiving area.

20. A method as claimed in claim 14 comprising in said speed regulating processor, executing a pattern recognition algorithm to identify said object that is positioned on the patient positioned on the patient examination table via the characteristic pattern.

21. A method as claimed in claim 20 comprising identifying said object by executing said pattern recognition algorithm dependent on a position of said object that is positioned on the patient positioned on said patient examination table.

22. A method as claimed in claim 14 comprising, via a user interface of said speed regulating processor, selecting a designation of said object from an object list prior to movement of the patient examination table into the patient receiving area, and regulating said speed of said patient examination table dependent on the selected object.

23. A method as claimed in claim 22 comprising setting a target position for positioning of said patient examination table dependent on the selection of said object, and optimizing said target position in said speed regulating processor dependent on the position data detected by the position data acquisition detector.

24. A non-transitory, computer-readable data storage medium encoded with programming instructions, said storage medium being loaded into a computer of a magnetic resonance (MR) apparatus that comprises an MR data acquisition scanner having a patient receiving area therein that has an isocenter, and having a movable patient examination table of a patient positioning device, and wherein said programming instructions cause said computer to:

operate the patient positioning device with a speed regulating processor of the computer to move the patient examination table, with an object that is positioned on a patient positioned thereon, into the patient receiving area at an initial speed, the object being a physical ancillary unit associated with the MR apparatus that is separate from the patient, the object including a predetermined characteristic pattern formed thereon;

operate a position data acquisition detector that is separate from the MR data acquisition scanner to detect position data associated with the object on the patient examination table by detecting the characteristic pattern on the object, while the patient examination table with the object thereon is moving in the patient receiving area;

in said speed regulating processor, evaluate the acquired position data to determine a distance of the object on the patient examination table in relation to the isocenter; and from said speed regulating processor, operate the patient positioning device to regulate the speed of movement of the patient examination table dependent on said distance of the object relative to the isocenter, by adjusting said initial speed, wherein the predetermined characteristic pattern formed on the object indicates a center and an edge region of the physical ancillary unit associated with the MR apparatus.

* * * * *